United States Patent [19]

Clark

[11] Patent Number: 5,407,926

[45] Date of Patent: * Apr. 18, 1995

[54] OPHTHALMIC COMPOSITION

[75] Inventor: Abbot F. Clark, Arlington, Tex.

[73] Assignee: Alcon Laboratories, Inc., Ft. Worth, Tex.

[*] Notice: The portion of the term of this patent subsequent to Jul. 31, 2007 has been disclaimed.

[21] Appl. No.: 966,118

[22] Filed: Oct. 23, 1992

Related U.S. Application Data

[63] Continuation of Ser. No. 555,692, Jul. 23, 1990, abandoned, which is a continuation-in-part of Ser. No. 399,351, Aug. 28, 1989, Pat. No. 4,945,089, which is a continuation of Ser. No. 139,222, Dec. 29, 1987, abandoned, and Ser. No. 419,226, Oct. 10, 1989, abandoned, which is a continuation of Ser. No. 264,918, Oct. 31, 1988, Pat. No. 4,876,250.

[51] Int. Cl.$^6$ .................... A61K 31/56; A61K 31/58
[52] U.S. Cl. .................... 514/179; 514/172; 514/173; 514/176; 514/180; 514/182
[58] Field of Search ............... 514/170, 183, 171, 180, 514/172, 173, 179, 176

[56] References Cited

U.S. PATENT DOCUMENTS

| 4,617,299 | 10/1986 | Knepper | 514/178 |
| 4,686,214 | 8/1987 | Boltralik | 514/179 |
| 4,876,250 | 10/1989 | Clark | 514/179 |

FOREIGN PATENT DOCUMENTS

| 0088462A3 | 9/1983 | European Pat. Off. . |
| 0250088 | 5/1987 | European Pat. Off. . |
| PCT/US86/-02189 | 10/1986 | WIPO . |

OTHER PUBLICATIONS

Gillman et al., "Goodman & Gillman's The Pharmacological Basis of Therapeutics", 7th Ed. 1473-1474 (1985).
McKerns, Steroid Hormones and Metabolism, Appleton-Century-Croffs, New York:1969, Chapter 8, pp. 93-103.
Kitazawa, Y., "Increased Intraocular Pressure Induced by Corticosteroids," Am. Journal of Oph., 82:492-493 (1976).
Cantrill et al., "Comparison of In Vitro Potency of Corticosteroids with Ability to Raise Intraocular Pressure," Am. Journal of Oph., 79:1012-1016 (1975).
Mindel et al., "Comparative Ocular Pressure Elevation by Medrysone, Fluorometholone, and Dexamethasone Phosphate," Arch Ophthal, 98:1577-1578 (1980).
Southren et al., "Intraocular Hypotensive Effect of a Topically Applied Cortisol Metabolite: 3α, 5β Tetrahydrocortisol," Investigative Ophthalmology & Visual Science, 28:901-903 (1987).
Treister et al., "Intraocular Pressure and Outflow Facility," Arch. Ophthal., 83:311-318 (1970).
Meyer et al., "Influence of Norethynodrel With Mestranol on Intraocular Pressure in Glaucoma," Arch Ophthal., 75:771-773 (1966).
Lamble et al., "Some Effects of Progestogens, Oestrogens and Androgens on the Ocular Tension of Rabbits and Owl Monkeys," Exp. Eye Res. 26:599-610 (1978).

(List continued on next page.)

Primary Examiner—Zohreh Fay
Attorney, Agent, or Firm—Julie J. L. Cheng; Gregg C. Brown

[57] ABSTRACT

Pharmaceutical compositions useful in the treatment of ophthalmic inflammation and methods of treating ophthalmic inflammation with those compositions are disclosed. The compositions contain a combination of a glucocorticoid and an angiostatic steroid. The angiostatic steroid substantially prevents any significant increases in intraocular pressure which might otherwise be experienced by the patient as a side effect of the glucocorticoid component of the compositions. The therapeutic interaction of the two components therefore allows the potent anti-inflammatory properties of the glucocorticoids to be utilized without fear of elevating intraocular pressure.

10 Claims, No Drawings

OTHER PUBLICATIONS of the Ocular Hypertension in Glaucoma," *Invest. Ophth. & Vis. Science,* 26:393–395 (Mar., 1985).

Knepper et al., "Intraocular Pressure & Glycosaminoglycan Distribution in the Rabbit Eye: Effect of Age and Dexamethosone," *Exp. Eye Res.,* 27:567–575 (1978).

Hester et al., "Steroid-Induced Ocular Hypertension in the Rabbit: A Model Using Subconjunctival Injections," *J. Ocular Pharmacology,* 3(3):185–189 (1987).

Crum et al., "A New Class of Steroids Inhibits Angiogenesis in the Presence of Heparin or a Heparin Fragment," *Science,* 230:1375–1378 (Dec., 1985).

Ingber et al., "A Possible Mechanism for Inhibition of Angiogenesis by Angiostatic Steroids: Induction of Capillary Basement Membrane Dissolution," *Endocrinology,* 119(4):176–1775 (1986).

Folkman et al., "Angiostatic Steroids," *Ann. Surg.,* 206(3):374–382 (1987).

Knepper et al. "Glycosaminoglycans and Outflow Pathways of the Eye and Brain," *Pediatric Neuroscience,* 12:240–251 (1985–86).

Knepper et al. "Effect of Dexamethasone, Progesterone, and Testosterone on IOP & GaGs in the Rabbit Eye," *Invest. Ophth. & Vis. Science,* 26:1093–1100 (Aug., 1985).

Rohen, Johanness W. "Why is Intraocular Pressure Elevated in Chronic Simple Glaucoma?", *Ophthalmology,* 90(7):758–764 (1983).

Southren et al. "5$\beta$–Dihydrocortisol: Possible Mediator

OPHTHALMIC COMPOSITION

This application is a continuation of application Ser. No. 07/555,692, filed Jul. 23, 1990, abandoned, which is a continuation-in-part of application Ser. No. 399,351, filed Aug. 28, 1989, (now U.S. Pat. No. 4,945,089), which is a continuation of application Ser. No. 139,222, filed Dec. 29, 1987, now abandoned, and application Ser. No. 419,226, filed Oct. 10, 1989, now abandoned, which is a continuation of application Ser. No. 264,918, filed Oct. 31, 1988, (now U.S. Pat. No. 4,876,250).

BACKGROUND OF THE INVENTION

Field of the Invention

The present invention relates to the field of ophthalmology. More particularly, this invention relates to the treatment of inflamed, ocular tissue.

Description of Related Art

Many compounds classified as glucocorticoids, such as dexamethasone and prednisolone, are very effective in the treatment of inflamed tissues, but in certain patients, these compounds cause elevations in intraocular pressure. Patients who experience elevations in intraocular pressure when treated with glucocorticoids are generally referred to as "steroid responders." The elevations in intraocular pressure are of particular concern in patients who are already suffering from elevated intraocular pressures, such as glaucoma patients. Moreover, there is always a risk that the use of glucocorticoids in patients who have normal intraocular pressures will cause elevations in pressure that may cause damage to ocular tissue. Since therapy with glucocorticoids is frequently long term (i.e., several days or more), there is potential for significant damage to ocular tissue as a result of prolonged elevations in intraocular pressure attributable to that therapy.

The following articles may be referenced for further background information concerning the well-recognized association between ophthalmic glucocorticoid therapy and elevations in intraocular pressure:

Kitazawa, "Increased Intraocular Pressure Induced by Corticosteroids," *Am. J. Ophthal.*, 82:492–493 (1976);

Cantrill, et al., "Comparison of In Vitro Potency of Corticosteroids with Ability to Raise Intraocular Pressure," *Am. J. Ophthal*, 79:1012–1016 (1975); and Mindel, et al., "Comparative Ocular Pressure Elevation by Medrysone, Fluorometholone, and Dexamethasone Phosphate," *Arch. Ophthal.*, 98:1577–1578 (1980).

One approach to solving the foregoing problems has been to search for compounds which are capable of alleviating ophthalmic inflammation without elevating intraocular pressure. The inventions described in commonly assigned U.S. Pat. No. 4,686,214 (Boltralik) and U.S. Pat. No. 5,223,493 (Boltralik) represent two examples of this approach. Notwithstanding the success of the therapies described in the above-cited inventions, there continues to be a need for still further improvements in the treatment of ophthalmic inflammation, such as an improvement which would allow potent glucocorticoids to be utilized to treat inflamed ocular tissue without fear of elevating intraocular pressure.

SUMMARY OF THE INVENTION

A principal objective of the present invention is the provision of a therapy for ophthalmic inflammation which allows the potent anti-inflammatory activity of the glucocorticoids to be employed without fear of elevating intraocular pressure. A further objective of the invention is the provision of methods of treatment and ophthalmic compositions useful in that therapy.

The foregoing objectives and other general objectives of the present invention are met by the provision of a therapy for ophthalmic inflammation wherein the elevations in intraocular pressure caused by glucocorticoids are substantially prevented. The therapy involves the combination of a first component, comprising an anti-inflammatory glucocorticoid and a second component, comprising one or more angiostatic steroids which prevent or antagonize the intraocular pressure elevating effect of the glucocorticoid. This combination allows the intraocular pressure ("IOP") elevating effect of glucocorticoids to be eliminated without adversely affecting the anti-inflammatory activity of the glucocorticoids. Thus, the therapy of the present invention makes it possible to employ the potent anti-inflammatory properties of the glucocorticoids without causing any significant elevations in intraocular pressure.

DESCRIPTION OF THE INVENTION

The present invention is based on the combination of one or more potent glucocorticoids with one or more angiostatic steroids. For purposes of the present invention, the term "angiostatic steroids" means steroids and steroid metabolites which inhibit angiogenesis.

The present invention is based on the finding that angiostatic steroids somehow inhibit the IOP elevating effect of glucocorticoids. The mechanism by which angiostatic steroids prevent or antagonize the IOP elevating effect of glucocorticoids is not totally understood at this point. While applicant does not wish to be bound by any theory, one possible explanation is that these compounds interfere with the action of glucocorticoids on trabecular meshwork cells, thereby blocking or reversing the IOP elevating effect of the glucocorticoids.

The angiostatic steroids utilized in the present invention include all pharmaceutically acceptable steroids and steroid metabolites which inhibit angiogenesis. The preferred angiostatic steroids have been previously disclosed in U.S. Pat. No. 86/02189, and have the following formula:

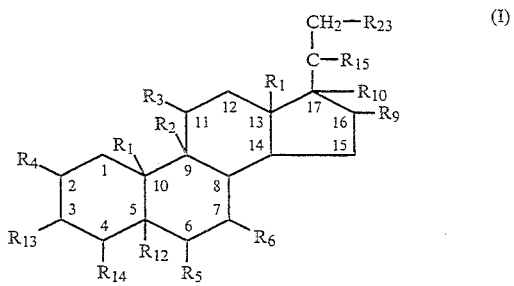

wherein:

$R_1$ is β—$CH_3$ or β—$C_2$;

$R_2$ is H or —Cl;

$R_3$ is H, =O, —OH, —O-alkyl($C_1$-$C_{12}$), OC(=O)alkyl($C_1$-$C_{12}$), —OC(=O)ARYL, —OC(=O)N(R)$_2$ or α—OC(=O)O$R_7$, wherein aryl is furyl, thienyl, pyrrolyl, or pyridyl and each of said moieties is optionally substituted with one or two ($C_1$-$C_4$)alkyl groups, or aryl is —($CH_2$)$_f$phenyl wherein f is an integer from 0 to 2 and the phenyl ring is optionally substituted with 1 to 3 groups selected from chlorine, fluorine, bromine, alkyl ($C_1-C_3$), alkoxy ($C_1-C_3$), thioalkoxy-($C_1-C_3$), $Cl_3C-$, $F_3C-$, $-NH_2$ and $-NHCOCH_3$ and R is hydrogen, alkyl ($C_1-C_4$), or phenyl and each R can be the same or different, and $R_7$ is aryl as herein defined, or alkyl ($C_1-C_{12}$); or $R_2$ and $R_3$ taken together are oxygen (—O—) bridging positions C-9 and C-11; or $R_2$ and $R_3$ taken together form a double bond between positions C-9 and C-11; or $R_2$ is α-F and $R_3$ is β—OH; or $R_2$ is α-Cl and $R_3$ is β-Cl; and $R_4$ is H, $CH_3$, Cl or F;

$R_5$ is H, OH, F, Cl, Br, $CH_3$, phenyl, vinyl or allyl;

$R_6$ is H or $CH_3$;

$R_9$ is H, OH, $CH_3$, F or $=CH_2$;

$R_{10}$ is H, OH, $CH_3$ or $R_{10}$ forms a second bond between positions C-16 and C-17;

$R_{12}$ is —H or forms a double bond with $R_{14}$;

$R_{13}$ is H, —OH, =O, —O—P(O)(OH)$_2$ or —O—C(=O)—(CH$_2$)$_t$COOH where t is an integer from 2 to 6:

$R_{14}$ is H or forms a double bond with $R_{12}$;

$R_{15}$ is =O or —OH; and $R_{23}$ with $R_{10}$ forms a cyclic phosphate as depicted by the following formula:

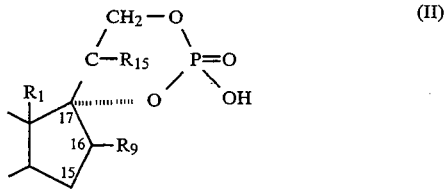

wherein $R_1$, $R_9$ and $R_{15}$ have the meaning defined above; or $R_{23}$ is —OH, O—C(=O)—$R_{11}$, —OP(O)—(OH)$_2$, or —O—C(=O)—(CH$_2$)$_t$COOH wherein t is an integer from 2 to 6; and $R_{11}$ is —Y—(CH$_2$)$_n$—X—(CH$_2$)$_m$—SO$_3$H, —Y'—(CH$_2$)p—X'—(CH$_2$)$_q$—NR$_{16}$R$_{17}$ or —Z(CH$_2$)$_r$Q, wherein Y is a bond or —O—; Y' is a bond, —O—, or —S—; each of X and X' is a bond, —CON(R$_{18}$)—, —N(R$_{18}$)CO—, —O—, —S—, —S(O)—, or —S(O$_2$)—; R$_{18}$ is hydrogen or alkyl ($C_1-C_4$); each of R$_{16}$ and R$_{17}$ is a lower alkyl group of from 1 to 4 carbon atoms optionally substituted with one hydroxyl or R$_{16}$ and R$_{17}$ taken together with the nitrogen atom to which each is attached forms a monocyclic heterocyclic selected from pyrrolidino, piperidino, morpholino, thiomorpholino, piperazino or N(lower)alkyl-piperazino wherein alkyl has 1 to 4 carbon atoms; n is an integer from 4 to 9; m is an integer from 1 to 5; p is an integer from 2 to 9: q is an integer from 1 to 5; wherein Z is a bond or —O—; r is an integer of from 2 to 9; and Q is one of the following:

(1) —R$_{19}$—CH$_2$COOH wherein R$_{19}$ is —S—, —S(O)—, —S(O)$_2$—, —SO$_2$N(R$_{20}$)—, or N(R$_{20}$)SO$_2$—; and R$_{20}$ is hydrogen or lower alkyl ($C_1-C_4$); with the proviso that the total number of carbon atoms in R$_{20}$ and (CH$_2$)$_r$ is not greater than 10; or (2) —CO—COOH; or (3) CON(R$_{21}$)CH(R$_{22}$)COOH wherein R$_{21}$ is H and R$_{22}$ is H, CH$_3$, —CH$_2$COOH, —CH$_2$CH$_2$COOH, —CH$_2$OH, —CH$_2$SH, —CH$_2$CH$_2$SCH$_3$, or —CH$_2$-Ph—OH wherein Ph—OH is p-hydroxyphenyl; or R$_{21}$ is CH$_3$ and R$_{22}$ is H; or R$_{21}$ and R$_{22}$ taken together are —CH$_2$CH$_2$CH$_2$—; or —N(R$_{21}$)CH(R$_{22}$)COOH taken together is —NHCH$_2$CONHCH$_2$COOH, with the proviso that except for the compound wherein $R_1$ is —CH$_3$, $R_2$ and $R_3$ taken together form a double bond between positions 9 and 11, $R_4$ and $R_6$ are hydrogen, $R_{12}$ and $R_{14}$ taken together form a double bond between positions 4 and 5, $R_5$ is β—F, $R_9$ is β—CH$_3$, $R_{10}$ is β—OH, $R_{13}$ and $R_{15}$ are =O and $R_{23}$ is —OP(o)—(OH)$_2$, $R_{13}$ is =O only when $R_{23}$ with $R_{10}$ forms the above described cyclic phosphate, and pharmaceutically acceptable salts thereof.

Excepted from the compounds of Formula (I) is the compound 3,11β, 17α, 21-tetrahydroxy-5 pregnane-20-one (the 3-alpha, 5-beta; 3-alpha, 5-alpha; 3-beta, 5-alpha; and 3-beta, 5-beta isomers of tetrahydrocortisol) wherein;

$R_{-15}$ is =O; $R_{10}$ is αOH;

$R_1$ is CH$_3$; $R_3$ is βOH; $R_2$ is H; $R_4$ is H; $R_{13}$ is m or —OH; $R_{14}$ is H;

$R_{12}$ is α or βH; $R_5$ is H; $R_6$ is H; $R_9$ is H and $R_{23}$ is OH.

Unless specified otherwise, all substituent groups attached to the cyclopenta phenanthrene moiety of Formula (I) may be in either the alpha or beta position. Additionally, the above structures include all pharmaceutically acceptable salts of the angiostatic steroids. The use of the above-described angiostatic steroids to control intraocular pressure is described in applicant's commonly assigned U.S. Pat. No. 4,876,250 issued Oct. 24, 1989; the entire contents of that patent are hereby incorporated in the present specification by reference.

Preferred angiostatic steroids of the above formula include:

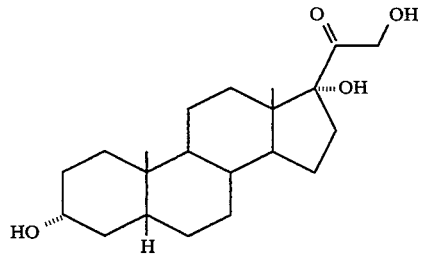

5β-pregnan-3α,17α,21-triol-20-one, which is also known as tetrahydrocortexolone, and its pharmaceutically acceptable salts;

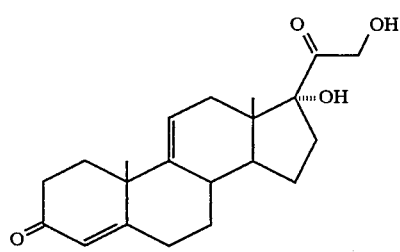

4,9(11)-pregnadien 17α,21-diol-3,20-dione, and its pharmaceutically acceptable salts; and

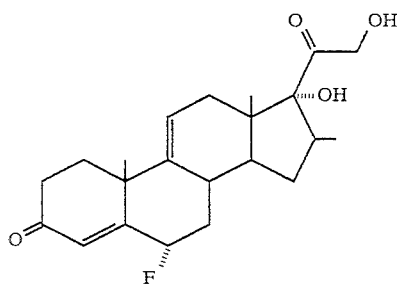

6-fluoro-17α,21-dihydroxy-16β-methyl-pregna-4,9(11)-diene-3,20-dione, and its pharmaceutically acceptable salts.

Tetrahydrocortexolone is a particularly preferred angiostatic steroid. It is a known compound. It has a molecular weight of 350.5 and an empirical formula of $C_{21}H_{34}O_4$. The compound is commercially available and may, for example, be obtained from Sigma Chemical Company, P.O. Box 14508, St. Louis, Mo. 63178 or Steraloids, Inc., P.O. Box 310, Wilton, N.H. 03086.

The above-described compounds may exist in several stereoisomeric forms. Specifically, with regard to stereoisometry, for tetrahydrocortexolone it refers to relative positions of the hydroxyl and hydrogen groups at the 3,5 positions, as to whether or not they are above or below the plane of the ring structure. Alpha position refers to below the plane of the ring structure, and beta refers to above the ring structure. Thus, tetrahydrocortexolone may exist as 3-alpha, 5-beta; 3-alpha, 5-alpha; 3-beta, 5-alpha; and 3-beta, 5-beta. The preferred isomer for use in this invention is 3-alpha, 5-beta-tetrahydrocortexolone. The ring containing the 1-5 positions is referred to as the "A-ring".

The glucocorticoids which may be employed in the present invention include all pharmaceutically acceptable compounds which are effective in the treatment of inflamed ocular tissue. The preferred glucocorticoids include dexamethasone, fluorometholone, medrysone, betamethasone, triamcinolone, prednisone, prednisolone, hydrocortisone, and pharmaceutically acceptable salts thereof. Further examples of glucocorticoids include prednicarbate, deflazacort, halomethasone, tixocortol, prednylidene (21-diethylaminoacetate), predníval, paramethasone, methylprednisolone, meprednisone, mazipredone, isoflupredone, halopredone acetate, halcinonide, formocortal, flurandrenolide, fluprednisolone, fluprednidine acetate, fluperolone acetate, fluocortolone, fluocortin butyl, fluocinonide, fluocinolone acetonide, flunisolide, flumethasone, fludrocortisone, fluclorinide, enoxolone, difluprednate, diflucortolone, diflorasone diacetate, desoximetasone (desoxymethasone), desonide, descinolone, cortivazol, corticosterone, cortisone, cloprednol, clocortolone, clobetasone, clobetasol, chloroprednisone, cafestol, budesonide, beclomethasone, amcinonide, allopregnane acetonide, alclometasone, 21-acetoxypregnenolone, tralonide, diflorasone acetate, deacylcortivazol, RU-26988, budesonide, and deacylcortivazol oxetanone. All of the above-cited glucocorticoids are known compounds. Further information about the compounds may be found, for example, in *The Merck Index*, Eleventh Edition (1989), and the publications cited therein, the entire contents of which are hereby incorporated in the present specification by reference.

In accordance with the present invention, antiinflammatory, ophthalmic compositions containing one or more glucocorticoids and one or more angiostatic steroids are provided. The compositions will contain one or more glucocorticoids in an anti-inflammatory effective amount and will contain one or more angiostatic steroids in an amount effective to inhibit the IOP elevating effect of the glucocorticoids. The amount of each component will depend on various factors, such as the relative tendency of certain glucocorticoids to cause IOP elevations, the severity and type of ocular inflammation being treated, the estimated duration of the treatment, and so on. In general, the ratio of the amount of glucocorticoid to the amount of angiostatic steroid on a weight to weight basis will be in the range of 10:1 to 1:20. The concentration of the glucocorticoid component will typically be in the range of about 0.01% to about 2.0% by weight. The concentration of the angiostatic steroid component will typically be in the range of about 0.05% to about 5.0% by weight.

The above-described active ingredients may be incorporated into various types of ophthalmic formulations for delivery to the eye. For example, the active ingredients may be combined with ophthalmologically acceptable preservatives, surfactants, viscosity enhancers, buffers, toxicity agents and water to form an aqueous, sterile ophthalmic suspension. In order to prepare sterile ophthalmic ointment formulations, the active ingredients are combined with a preservative in an appropriate vehicle, such as mineral oil, liquid lanolin, or white petrolatum. Sterile ophthalmic gel formulations may be prepared by suspending the active ingredient in a hydrophilic base prepared from the combination of Carbopol-940 (a carboxy vinyl polymer available from the B.F. Goodrich Company) according to published formulations for analogous ophthalmic preparations; preservatives and tonicity agents can also be incorporated. The specific type of formulation selected will depend on various factors, such as the severity and type of ophthalmic inflammation being treated, and dosage frequency. Ophthalmic solutions, suspensions, ointments and gels are the preferred dosage forms, and topical application to the inflamed ocular tissue is the preferred route of administration.

The following Example is presented to illustrate further the compositions of the present invention.

EXAMPLE

The following formulation is representative of the antiinflammatory compositions of the present invention.

| Ingredient | Amount (wt. %) |
| --- | --- |
| Tetrahydrocortexolone | 1.0 |
| Dexamethasone | 0.1 |
| Tyloxapol | 0.01 to 0.05 |
| HPMC | 0.5 |
| Benzalkonium chloride | 0.01 |
| Sodium chloride | 0.8 |
| Edetate Disodium | 0.01 |
| NaOH/HCl | q.s. pH 7.4 |
| Purified water | q.s. 100 mL |

The above formulation is prepared by first placing a portion of the purified water into a beaker and heating to 90° C. The hydroxypropylmethylcellulose (HPMC) is then added to the heated water and mixed by means of vigorous vortex stirring until all of the HPMC is dispersed. The resulting mixture is then allowed to cool while undergoing mixing in order to hydrate the HPMC. The resulting solution is then sterilized by means of autoclaving in a vessel having a liquid inlet and a hydrophobic, sterile air vent filter.

The sodium chloride and the edetate disodium are then added to a second portion of the purified water and dissolved. The benzalkonium chloride is then added to the solution, and the pH of the solution is adjusted to 7.4 with 0.1M NaOH/HCl. The solution is then sterilized by means of filtration.

The tetrahydrocortexolone and dexamethasone are sterilized by either dry heat or ethylene oxide. If ethylene oxide sterilization is selected, aeration for at least 72 hours at 50° C. is necessary. The sterilized THS and dexamethasone are weighed aseptically and placed into a pressurized ballmill container. The tyloxapol, in sterilized aqueous solution form, is then added to the ballmill container. Sterilized glass balls are then added to the container and the contents of the container are milled aseptically at 225 rpm for 16 hours, or until all particles are in the range of approximately 5 microns.

Under aseptic conditions, the micronized drug suspension formed by means of the preceding step is then poured into the HPMC solution with mixing. The ballmill container and balls contained therein are then rinsed with a portion of the solution containing the sodium chloride, the edetate disodium and benzalkonium chloride. The rinse is then added aseptically to the HPMC solution. The final volume of the solution is then adjusted with purified water and, if necessary, the pH of the solution is adjusted to pH 7.4 with NaOH/HCl.

The treatment method of the present invention comprises application of an effective amount of the above-described compositions to the eye. The dosage regimen utilized will depend on the severity and type of inflammation being treated, as well as various clinical factors, such as, the patient's age, sex, weight and medical history. In general, the above-described compositions may be topically applied, for example, as drops to the upper globe, or as a 0.5–1 cm strip of ointment or gel to the lower conjunctival sac of the eye. Suspensions will generally be applied 1 to 4 times daily, while ointments or gels will generally be applied once or twice daily. The application of sustained release formulations (e.g., polymer based gels) once daily at bedtime will be preferred in some conditions. Intraocular routes of administration, such as injections or instillations in conjunction with intraocular surgery, are also contemplated.

What is claimed is:

1. A method of treating ophthalmic inflammation which comprises topical application of a therapeutically effective amount of a pharmaceutical composition to an affected eye, wherein the topical application of said composition does not significantly increase the intraocular pressure of the affected eye, said composition comprising an anti-inflammatory effective amount of a glucocorticoid, an amount of an angiostatic steroid effective to inhibit the glucocorticoid from elevating the intraocular pressure of asteroid responder and a pharmaceutically acceptable carrier therefore; wherein the angiostatic steroid has the following formula or is a pharmaceutically acceptable salt thereof:

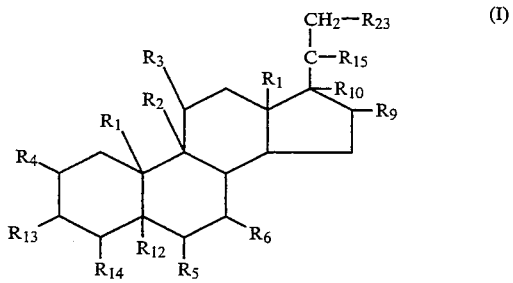

wherein:
$R_1$ is $\beta$—$CH_3$ or $\beta$—$C_2H_5$;
$R_2$ is H or Cl;
$R_3$ is H, =O or OH;
$R_2$ and $R_3$ taken together are oxygen (—O—) bridging positions C-9 and C-11; or
$R_2$ and $R_3$ taken together form a double bond between positions C-9 and C-11; or
$R_2$ is $\alpha$—F and $R_3$ is $\beta$—OH; or
$R_2$ is $\alpha$—Cl and $R_3$ is $\beta$—Cl; and
$R_4$ is H, $CH_3$, Cl or F;
$R_5$ is H, OH, F, Cl, Br, $CH_3$, phenyl, vinyl or allyl;
$R_6$ is H or $CH_3$;
$R_9$ is H, OH, $CH_3$, F or =$CH_2$;
$R_{10}$ is H, OH, $CH_3$ or forms a second bond between positions C-16 and C-17;
$R_{12}$ is H or forms a double bond with $R_{14}$;
$R_{13}$ is H, OH, =O, —O—P(O)—(OH)$_2$ or —O—C(=O)—(CH$_2$)$_t$COOH, where t is an integer from 2 to 6;
$R_{14}$ is H or forms a double bond with $R_{12}$;
$R_{15}$ is =O or OH; and
$R_{23}$ with $R_{10}$ forms a cyclic phosphate as depicted by the following formula:

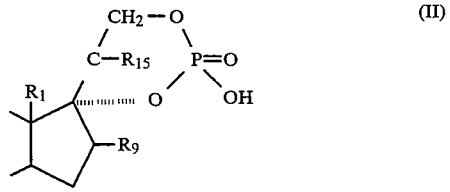

wherein $R_1$, $R_9$ and $R_{15}$ have the meanings defined above; or
$R_{23}$ is OH, —O—P(O)—(OH)$_2$ or —O—C(=O)—(CH$_2$)$_t$COOH wherein t is an integer from 2 to 6;
with the proviso that, except for the compound wherein $R_1$ is $CH_3$, $R_2$ and $R_3$ taken together form a double bond between positions 9 and 11, $R_4$ and $R_6$ are hydrogen, $R_{12}$ and $R_{14}$ taken together form a double bond between positions 4 and 5, $R_5$ is $\alpha$—F, $R_9$ is $\beta$—$CH_3$, $R_{10}$ is $\alpha$—OH, $R_{13}$ and $R_{16}$ are =O and $R_{23}$ is —O—P(O)—(OH)$_2$, $R_{13}$ is =O only when $R_{23}$ with $R_{10}$ forms the above-described cyclic phosphate; and excluding the compounds wherein $R_{16}$ is =O, $R_{10}$ is $\alpha$—OH, $R_1$ is $CH_3$, $R_3$ is $\beta$—OH or H, $R_2$ is H, $R_4$ is H, $R_{13}$ is $\alpha$- or $\beta$—OH, $R_{14}$ is H, $R_{12}$ is $\alpha$- or $\beta$—H, $R_5$ is H, $R_6$ is H, $R_9$ is H and $R_{23}$ is OH.

2. The method of claim 1, wherein the angiostatic steroid is selected from the group consisting of: 4,9(11)-pregnadien-17$\alpha$,21-diol-3,20-dione; 4-pregnen-11$\beta$,17$\alpha$,20$\beta$,21-tetrol-3-one; 5$\beta$-pregnan-3$\alpha$,17$\alpha$-diol- 20-one; 4-pregnen-17α-ol-3,20-dione; 4-pregnen-11β,17α,20α,21-tetrol-3-one; 5β-pregnan-3α,17α,21-triol-20-one; 1,4,9(11)-pregnatrien-17α,21-diol-3,20-dione; 6α-fluoro-17α,21-dihydroxy-16β-methyl-pregna-4,9(11)-diene-3,20-dione; or pharmaceutically acceptable salts thereof.

3. The method of claim 2, wherein the angiostatic steroid is selected from the group consisting of: 4,9(11)-pregnadien-17α,21-diol-3,20-dione; 5β-pregnan-3α,17α-diol-20-one; 4-pregnen-17α-ol-3,20-dione; 5β-pregnan-3α,17α,21-triol-20-one; 6α-fluoro-17α,21-dihydroxy-16β-methyl-pregna-4,9(11)-diene-3,20-dione; or pharmaceutically acceptable salts thereof.

4. The method of claim 3, wherein the angiostatic steroid comprises tetrahydrocortexolone or a pharmaceutically acceptable salt thereof.

5. The method of claim 3, wherein the angiostatic steroid comprises 6α-fluoro-17α,21-dihydroxy-16β-methyl-pregna-4,9(11)-diene-3,20-dione, or a pharmaceutically acceptable salt thereof.

6. The method of claim 3, wherein the angiostatic steroid comprises 4,9(11)-pregnadien 17α,21-diol-3,20-dione, or a pharmaceutically acceptable salt thereof.

7. The method of claim 1, wherein the glucocorticoid is selected from dexamethasone, fluorometholone, medrysone, betamethasone, triamcinolone, prednisone, prednisolone, hydrocortisone, and pharmaceutically acceptable salts thereof.

8. The method of claim 1, wherein the ratio of the amount of the glucocorticoid to the amount of an angiostatic steroid on a weight to weight basis in the range of 10:1 to 1:20.

9. The method of claim 1, wherein the glucocorticoid is contained in the composition in an amount in the range of about 0.01% to about 2.0% by weight.

10. The method of claim 1, wherein the angiostatic steroid is contained in the composition in an amount in the range of about 0.05% to about 5.0% by weight.

* * * * *